(12) United States Patent
Favier et al.

(10) Patent No.: US 9,918,856 B2
(45) Date of Patent: Mar. 20, 2018

(54) STENT SPACER

(71) Applicants: Universite Joseph Fourier, Grenoble (FR); Centre National de la Recherche Scientifique, Paris (FR); Assistance Publique—Hopitaux De Paris, Paris (FR)

(72) Inventors: Denis Favier, Grenoble (FR); Pierre Mozer, Paris (FR); Yohan Payan, Paris (FR); Gabriel Antherieu, Grenoble (FR); Nathanael Connesson, Grenoble (FR)

(73) Assignee: Universite Grenoble Alpes, Saint Martin D' Heres (FR)

( * ) Notice: Subject to any disclaimer, the term of this patent is extended or adjusted under 35 U.S.C. 154(b) by 0 days.

(21) Appl. No.: 14/900,346

(22) PCT Filed: Jun. 20, 2014

(86) PCT No.: PCT/FR2014/051547
§ 371 (c)(1),
(2) Date: Dec. 21, 2015

(87) PCT Pub. No.: WO2014/202917
PCT Pub. Date: Dec. 24, 2014

(65) Prior Publication Data
US 2016/0151179 A1    Jun. 2, 2016

(30) Foreign Application Priority Data

Jun. 21, 2013 (FR) ..................... 13 55935

(51) Int. Cl.
*A61F 2/88* (2006.01)
*A61M 27/00* (2006.01)

(52) U.S. Cl.
CPC ............. *A61F 2/88* (2013.01); *A61M 27/008* (2013.01); *A61F 2210/0019* (2013.01);
(Continued)

(58) Field of Classification Search
CPC .... A61F 2/82–2/945; A61F 2250/0042; A61F 2210/0023–2210/0052
See application file for complete search history.

(56) References Cited

U.S. PATENT DOCUMENTS 5,562,641 A * 10/1996 Flomenblit ............... A61F 2/88
                                                               604/104
6,077,298 A *  6/2000 Tu ............................. A61F 2/82
                                                              623/1.19

(Continued)

FOREIGN PATENT DOCUMENTS

WO    WO 02/036045 A2    5/2002
WO    WO 2006/086304 A1  8/2006

OTHER PUBLICATIONS

International Search Report, dated Aug. 18, 2014, from corresponding International Application No. PCT/FR2014/051547.

(Continued)

*Primary Examiner* — Yashita Sharma
(74) *Attorney, Agent, or Firm* — Wolf, Greenfield & Sacks, P.C.

(57) ABSTRACT

A spacer including a first part made from a first shape memory material, and a second part made from a second shape memory material.

10 Claims, 1 Drawing Sheet

(52) U.S. Cl.
CPC ............... *A61F 2210/0033* (2013.01); *A61F 2250/0039* (2013.01); *A61F 2250/0042* (2013.01); *A61F 2310/00023* (2013.01)

(56) References Cited

U.S. PATENT DOCUMENTS

| | | | |
|---|---|---|---|
| 6,413,273 B1 * | 7/2002 | Baum ..................... | A61F 2/88 606/198 |
| 2002/0142119 A1 | 10/2002 | Seward et al. | |
| 2003/0009215 A1 * | 1/2003 | Mayer ..................... | A61F 2/90 623/1.22 |
| 2004/0199246 A1 * | 10/2004 | Chu ........................ | A61F 2/90 623/1.32 |
| 2006/0287708 A1 * | 12/2006 | Ricci ...................... | A61F 2/91 623/1.15 |
| 2009/0204200 A1 * | 8/2009 | Bales, Jr. ................ | A61F 2/88 623/1.16 |
| 2013/0041454 A1 | 2/2013 | Dobson et al. | |

OTHER PUBLICATIONS

Translation of the Written Opinion of the International Searching Authority, dated Dec. 21, 2015 from corresponding International Application No. PCT/FR2014/051547.

* cited by examiner and second material is activated.

STENT SPACER

CROSS-REFERENCE TO RELATED APPLICATIONS

This application is the national phase of International Application No. PCT/FR2014/051547, titled, filed on Jun. 20, 2014, which claims the priority benefit to French Application No. 13/55935, filed on Jun. 21, 2013, which applications are hereby incorporated by reference to the maximum extent allowable by law.

The present patent application claims the priority benefit of French patent application FR13/55935 which is herein incorporated by reference.

BACKGROUND

The present application generally relates to the field of spacers or extensors, and more particularly aims at the field of vascular or urethral retractors usually called stent in the art.

DISCUSSION OF THE RELATED ART

To maintain open and/or enlarge the lumen of certain ducts or vessels of the human body narrowed or obstructed by diseases, it is known to insert into the duct a tubular prosthesis usually called stent. During a phase of positioning the stent in the duct, the stent is in a contracted configuration where its diameter is much smaller than the duct diameter, which enables it to freely displace within the duct. Once the stent has been positioned at the desired location, a step of stent expansion, during which the stent is radially stretched to a diameter of the same order s that of the duct, or even slightly greater than that of the duct, to enlarge the opening of the narrowed area of the duct. The stent may be left in place for the time necessary to treat the causes of the duct narrowing. In many cases, it should however be removed after the treatment.

A disadvantage of known stents is that their removal is relatively complex and may cause lesions of the duct.

SUMMARY

An object of an embodiment is to provide a stent overcoming all or part of the disadvantages of known stents.

An object of an embodiment is to provide a stent simpler to extract from a duct than known stents.

Thus, an embodiment provides a stent comprising a first portion made of a first shape-memory material, and a second portion made of a second shape-memory material.

According to an embodiment, the first shape-memory material has a first activation temperature, and the second shape-memory material has a second activation temperature higher than the first temperature.

According to an embodiment, the first and second portions are arranged so that the stent takes a first configuration when the first material is activated, and a second configuration when the second material is activated.

According to an embodiment, the first shape-memory material is a superelastic material, and the second shape-memory material memorizes a thermally-activatable shape.

According to an embodiment, the first and second portions are arranged so that the stent takes a first configuration when the second material is not activated, and a second configuration when the second material is activated.

According to an embodiment, at least one section of the stent has an approximately generally cylindrical shape having a first diameter in the first configuration and a second diameter smaller than the first diameter in the second configuration.

According to an embodiment, the first and second portions are part of a same filiform element of generally helical shape.

According to an embodiment, the filiform element has the shape of a diabolo.

According to an embodiment, the first portion is a hollow wire, and the second portion is a wire of smaller diameter arranged within the hollow wire.

According to an embodiment, the first and second portions are separate areas of the cross-section of a same wire.

According to an embodiment, the first and second shape-memory materials are alloys based on nickel and on titanium.

According to an embodiment, the stent comprises contact terminals enabling to apply an electric current in the first and/or second portions.

According to an embodiment, the stent further comprises a silicone coating.

Another embodiment provides a method of using the above-mentioned stent, comprising a step of positioning the stent in a duct or a cavity in a first configuration at a temperature lower than the activation temperature of the second shape-memory material.

According to an embodiment, the method further comprises a step of heating the stent to the second temperature, followed by a step of removing the stent from the duct or the cavity.

BRIEF DESCRIPTION OF THE DRAWINGS

The foregoing and other features and advantages will be discussed in detail in the following non-limiting description of specific embodiments in connection with the accompanying drawings, among which.

Figure 1:
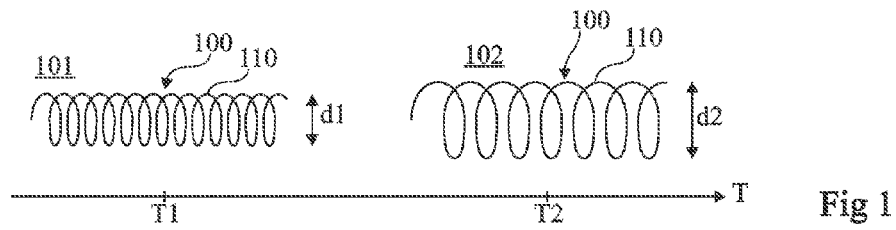
FIG. 1 schematically shows the operation of an example of a stent.

For clarity, the same elements have been designated with the same reference numerals in the different drawings. Further, only those elements which are useful to the understanding of the present invention have been shown and will be described. In particular, the tools capable of being used to place and/or remove a stent have neither been described in detail nor shown, the described embodiments being compatible with usual stent placing and removal tools, or the forming of stent placing and removal tools compatible with the described embodiments being within the abilities of those skilled in the art.

DETAILED DESCRIPTION

It has already been provided to form a stent made of a shape-memory material, that is, a material having the ability of memorizing a shape and, after a deformation, of almost instantaneously returning thereto when its temperature exceeds a transition or activation temperature.

FIG. 1 schematically shows the operation of a shape-memory stent. Stent 100 of FIG. 1 comprises a continuous wire 110 of helical shape made of a shape-memory material, for example, a nickel-titanium alloy, having an activation temperature T2.

Before a phase of inserting the stent into a duct (not shown), the stent is shaped in a configuration 101 where the stent has a generally cylindrical shape of diameter d1 smaller than the normal diameter of the duct, that is, than the diameter of the duct in the absence of a narrowing due to a disease. The stent is inserted into the duct in configuration 101 and positioned at the desired location, for example, by means of a catheter (not shown).

Once it has been properly positioned in the duct, the stent is expanded and takes a configuration 102 where the stent has a generally cylindrical shape of diameter d2 greater than diameter d1. If activation temperature T2 of the shape-memory material is lower than the temperature of the human or animal body having the stent introduced into it, the expansion may be obtained by expelling the stent (in its activated shape) from the catheter, by taking advantage of the superelasticity specific to shape-memory materials. If temperature T2 of activation of the shape-memory material is higher than the temperature of the human or animal body having the stent introduced into it, the stent may, once properly positioned in the duct, be heated up to a temperature higher than or equal to temperature T2. To achieve this, an aqueous solution heated at a temperature greater than or equal to temperature T2 may be injected into the duct.

Diameter d2 is for example of the same order as the normal diameter of the duct or slightly greater than the normal diameter of the duct, which may enable to enlarge the lumen of the narrowed portion of the duct at the stent level. The shape of the stent in configuration 102 corresponds to the shape memorized by shape-memory wire 110, or memory shape of the stent. The shape-memory material may be selected to be such that its activation temperature T2 is greater than the temperature of the human or animal body, for example, in the range from 40 to 45° C., to avoid an unwanted activation of the stent during its insertion into the duct. After its activation, the stent remains in configuration 102 even when its temperature falls back under temperature T2, due to the hysteresis properties of the shape-memory material.

To remove the stent after a disease treatment step, it may be provided to force unwind the helical wire forming it. However, a disadvantage is that the risk of lesion of the duct on removal thereof is relatively high.

As a variation, to remove the stent, it may be provided to cool it down to a deactivation temperature T1, lower than temperature T2, at which the shape-memory material remains in the radially stretched shape of configuration 102 but acquires a larger deformability than at the temperature of the human or animal body, thus enabling to remove the stent by unwinding the helical wire while decreasing risks of duct lesion.

The shape-memory material may be selected to be such that its deactivation temperature T1 is much lower than the temperature of the human or animal body, for example, in the order of 25° C., to avoid an unwanted deactivation of the stent. To cool down the stent, an aqueous solution at low temperature (lower than or equal to T1) may be injected in the vicinity of the stent, for example, via a catheter. However, a disadvantage is that the injection of a cold fluid in the vicinity of the stent is a relatively complex operation and may be a problem.

An object of the described embodiments is to provide a shape-memory stent which overcomes all or part of the above-mentioned disadvantages.

Figure 2:
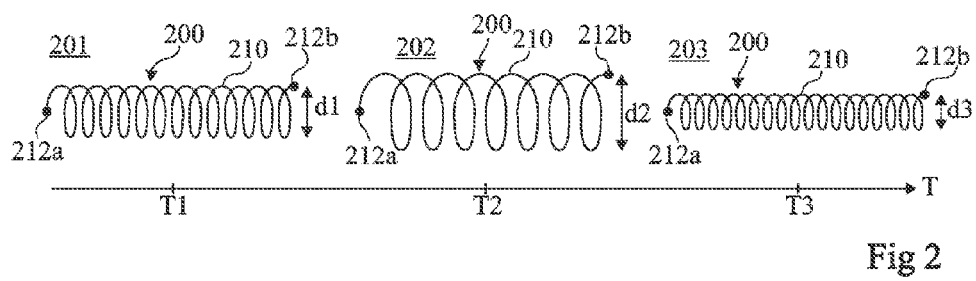
FIG. 2 schematically shows the operation of an embodiment of a stent.

FIG. 2 schematically shows the operation of an embodiment of a stent 200. Stent 200 comprises a filiform element 210 shaped according to a substantially helical general configuration, having shape-memory properties.

Before a phase of inserting the stent into a duct (not shown), the stent is shaped in a configuration 201 where the stent has a generally cylindrical shape of diameter d1 smaller than the normal diameter of the duct. The stent is inserted into the duct with configuration 201 and positioned at a desired location of the duct, for example, by means of a catheter (not shown).

Once it has been properly positioned in the duct, the stent is heated up to a temperature higher than or equal to a first temperature T2 of activation of element 210. To achieve this, a fluid heated up to a temperature T2 may be injected into the duct. However, in a preferred embodiment, it is provided to heat the stent by Joule effect by circulating an electric current in element 210. This provides a heating which is simpler to implement and more efficient than a heating by fluid injection. This further enables to limit risks of burns with respect to a heating by fluid injection. To allow the application of an electric heating current, element 210 may comprise two contact terminals 212a and 212b respectively connected to its to ends. The electric heating current is for example provided by a cell or battery coupled to a tool for inserting the stent into the duct. According to the envisaged used, a conductive wire (not shown in the drawings) may be provided to bring one of contact terminals 212a, 212b close to the other, to ease the application of the electric heating current.

When the stent reaches temperature T2, it takes a configuration 202 where the stent has a generally cylindrical shape of diameter d2 greater than diameter d1. Diameter d2 is for example of the same order of magnitude as the normal diameter of the duct or slightly greater than the normal diameter of the duct, which may enable to enlarge the lumen of the duct at the stent level. The shape of the stent in configuration 202 corresponds to a first shape memorized by element 210, or first memory shape of the stent. Element 210 may be selected to be such that its first activation temperature T2 is higher than the temperature of the human or animal body, for example, in the range from 40 to 45° C., to avoid an unwanted activation of the stent during its insertion into the duct. After its first activation, the stent remains in configuration 202 even when its temperature falls back under temperature T2, due to the hysteresis properties of the shape-memory material.

To remove the stent, it is provided to heat it up to a temperature greater than or equal to a second activation temperature T3 of element 210, higher than temperature T2. To achieve this, a fluid heated up to a temperature higher than or equal to temperature T3 may be injected into the duct. However, in a preferred embodiment, it is provided to heat the stent by Joule effect by circulating an electric current in element 210. The electric heating current is for example supplied by a cell or a battery coupled to a stent extraction tool.

When the stent reaches temperature T3, it contracts to a configuration 203 where the stent has a generally cylindrical shape of diameter d3 smaller than diameter d2. Diameter d3 is for example of the same order of magnitude as diameter d1 of configuration 201, or smaller than diameter d1. In any case, diameter d3 is smaller than the normal diameter of the duct. The shape of the stent in configuration 203 corresponds to a second shape memorized by element 210, or second memory shape of the stent. Element 210 may be selected so that its second activation temperature T3 is significantly higher than temperature T2, to avoid an incidental contraction of the stent in configuration 203 when the stent is heated to be deployed in configuration 202. Temperature T3 is however preferably selected to be sufficiently low to avoid for the patient to be burnt on removal of the stent. As an example, element 210 is such that its second activation temperature T3 is in the range from 50 to 60° C. After its second activation, the stent remains in configuration 203 even when its temperature falls back below temperature T3, due to the hysteresis properties of the shape-memory material.

When the stent is in configuration 203, it may freely circulate in the duct, which enables to smoothly remove it with no risk of lesion of the duct.

Figure 3:
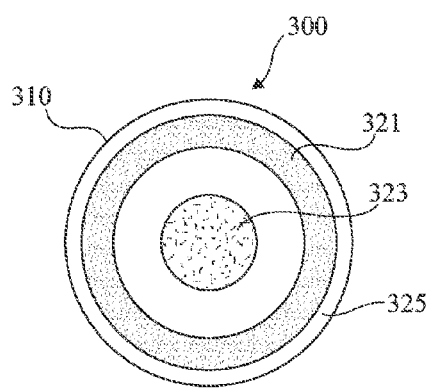
FIG. 3 is a partial cross-section view illustrating in further detail a preferred embodiment of a stent compatible with the operation of FIG. 2.

FIG. 3 is a partial cross-section view illustrating in further detail a preferred embodiment of a stent 300 compatible with the operation described in relation with FIG. 2, that is, capable of expanding to a first configuration at a first activation temperature T2 and of contracting to a second configuration at a second activation temperature T3 higher than temperature T2. As in the example of FIG. 2, stent 300 comprises a filiform element 310 of substantially helical general shape (not shown in FIG. 3), having shape-memory properties. The described embodiments are however not limited to a stent of helical shape, and other shapes may be provided according to the envisaged use. In FIG. 3, only a cross-section of filiform element 310 has been shown.

Element 310 comprises a hollow wire or tube 321 made of a first shape-memory material and, inside of hollow wire 321, a solid wire 323 made of a second shape-memory material. Wires 321 and 323 have approximately the same length, which approximately corresponds to the length of unwound element 310. Wires 321 and 323 are preferably metallic to allow the circulation of an electric current of activation of the stent by Joule effect in element 310. Wires 321 and 323 may be made mechanically and/or electrically attached to each other at their ends and/or along all or part of their length, for example, by friction, welding, etc.

As an example, hollow wire 321 is treated to memorize a shape corresponding to configuration 202 of FIG. 2 and to activate at temperature T2, and solid wire 323 is treated to memorize another shape corresponding to configuration 203 of FIG. 2 and to activate at temperature T3. The treatments applied to wires 321 and 323 to obtain the desired memory shapes and activation temperatures will not be described in detail herein, such treatments being within the abilities of those skilled in the art. As an example, wires 321 and 323 may be made of a same initial material, for example, a same nickel-titanium alloy, after which different thermal treatments may be applied to wires 321 and 323 to modify by different proportions the atom bonds or the atom compositions of the alloy in the two wires to obtain the desired properties.

In the shown example, element 310 further comprises a sheath 325 coating the outer wall of hollow wire 321. Sheath 325 is made of a material selected to prevent or to limit possible phenomena of encrustation of the stent in the duct walls, and to ease the extraction of the stent. Sheath 325 is preferably electrically and thermally insulating to decrease electrocution or burning risks for the patient in case of an activation of the stent by application of an electric current in the stent. Sheath 325 is for example made of silicone. It should be noted that sheath 325 may be replaced or completed with a skirt made of an insulating material, for example, made of silicone, coating the external wall of the generally cylindrical shape defined by the stent.

An advantage of the embodiment of FIG. 3 is that stent 300 is relatively simple to form.

Figure 4:
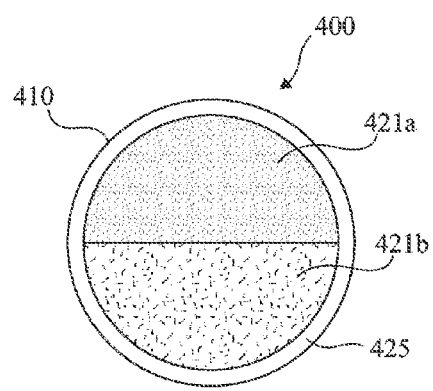
FIG. 4 is a partial cross-section view illustrating in further detail another embodiment of a stent compatible with the operation of FIG. 2.

FIG. 4 is a partial cross-section view illustrating another embodiment of a stent 400 compatible with the operation described in relation with FIG. 2. As in the example of FIG. 2, stent 400 comprises a filiform element 410 of substantially helical general shape (not shown in FIG. 4), having shape-memory properties. In FIG. 4, only a cross-section of filiform element 410 has been shown.

Element 410 comprises a wire 421, for example, a solid wire, having in cross-section two areas 421a and 421b made of different shape-memory materials. Areas 421a and 421b for example extend along the entire length of wire 421. The described embodiments are however not limited to this specific case. Wire 421 is preferably metallic to allow the circulation, in element 410, of an electric current for activating the stent by Joule effect.

As an example, area 421a is treated to memorize a shape corresponding to configuration 202 of FIG. 2 and to activate at temperature T2, and area 421b is treated to memorize another shape corresponding to configuration 203 of FIG. 2 and to activate at temperature T3.

As an example, to form wire 421, it is started from a wire made of a single material, for example, a nickel-titanium alloy, and the entire wire is treated to memorize a first shape and to activate at temperature T2. After this first treatment, the wire may be shaped according to a second shape different from the first shape, and locally treated so that only area 421b of the wire cross-section memorizes the second shape and acquires an activation temperature T3 higher than temperature T2. This local treatment of the wire cross-section is for example performed by means of a laser beam heating a single side of the wire along the entire wire length. Other treatment methods may be envisaged to obtain the desired result. As an example, nickel may be diffused on a single side of the wire. To achieve this, an element having a high nickel content may be placed on a single side of the wire, the assembly being heated at high temperature.

It should be noted that, although a clear separation of areas 421a and 421b has been shown in FIG. 4, in practice, according to the treatment method used, the shape-memory properties of element 410 may gradually vary between areas 421a and 421b of wire 421.

It should further be understood that the embodiment of FIG. 4 may apply not only to a solid wire 421, as has just been described, but also to a hollow wire.

In the shown example, element 410 further comprises a sheath 425, for example, made of silicone, coating the outer wall of wire 421.

Figure 5:
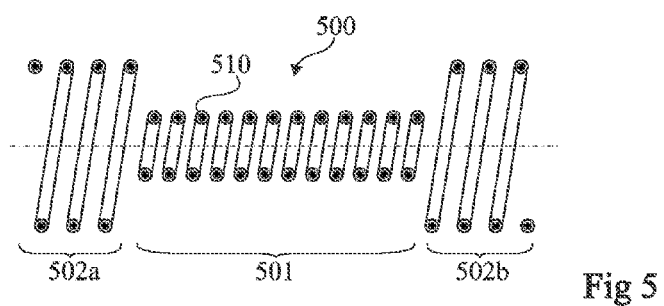
FIG. 5 is a cross-section view illustrating an example of the general shape that a stent of the type described in relation with FIGS. 2 to 4 may have.

FIG. 5 is a cross-section view along a longitudinal plane of a stent 500, illustrating an example of the general shape that a stent of the type described in relation with FIGS. 2 to 4 may have. As in the example of FIGS. 2 to 4, stent 500 comprises a filiform element 510 of substantially helical general shape. To avoid unwanted migrations of the stent after it has been deployed in a duct, stent 500 has a diabolo shape, that is, it comprises a substantially cylindrical central section 501 and, on either side of section 501, cylindrical sections 502a and 502b having diameters greater than the diameter of section 501. The described embodiments are however not limited to this specific example. Other stent shapes may be envisaged (widening on a single side, number of different diameters greater than two, etc.).

An advantage of the embodiments described in relation with FIGS. 2 to 5 is that the described stents may easily be inserted into and extracted from a duct with no risk of lesion of this duct.

Further, the stent may be inserted and extracted without requiring the injection of a heating or cooling fluid in the vicinity of the stent, which greatly simplifies stent placing and removal operations and avoids risks of burns or contamination for the patient.

The described embodiments are particularly adapted for a use in the urethra when the urethral canal is narrowed or obstructed by the prostate due to a hypertrophy of the prostate.

It is thus provided to use a stent of the type described in relation with FIGS. 2 to 5 to increase the lumen of the urethral canal when the latter is narrowed or obstructed due to a hypertrophy of the prostate.

The described embodiments may however also be used in other canals, ducts, or cavities of the human or animal body.

In the above-described embodiments, stents are formed from a filiform element (respectively 310 and 410 in FIGS. 3 and 4) comprising, longitudinally, two portions (321 and 323 in FIG. 3 and 421a and 421b in FIG. 4) made of shape-memory materials treated differently, each portion memorizing a shape of the stent and activating (that is, recovering its memorized shape) when it is heated up to its activation temperature.

It should however be noted that expression "shape-memory material" designates not only materials capable of memorizing a shape and of returning thereto when their temperature exceeds a so-called activation temperature, but also materials capable of being treated to acquire so-called superelasticity properties in a range of temperatures of use. The shape-memory materials treated in superelasticity have no specific activation temperature, but are capable of reversibly undergoing a significant deformation under the effect of stress in the considered temperature range.

As an alternative embodiment, it may be provided, in the above-described embodiments, to form one of the two shape-memory portions of the stent (for example, portion 321 in FIG. 3 and portion 421a in FIG. 4) with a shape-memory material treated to acquire superelastic properties at the temperature of the human or animal body into which the stent is intended to be inserted. The superelasticity of the first material may be taken advantage of during the stent insertion phase, and the shape memorized by the second material may be exploited on removal of the stent.

In this case, the stent for example has the following operation:

On insertion thereof into a duct, the stent is stressed to a configuration corresponding to configuration 201 of FIG. 2 (superelastic deformation), for example, by means of a tool, for example, a catheter, comprising hooks enabling to apply the desired stress.

Once the stent has been properly positioned in the duct, the stress is released, and the stent relaxes, like a spring, to return to a shape corresponding to configuration 202 of FIG. 2 (reversibility of the superelastic deformation).

To remove the stent, it is provided to heat it up to a temperature higher than or equal to the activation temperature of the second shape-memory material (portion 323 of the stent in FIG. 3 or portion 421b of the stent in FIG. 4). The stent then contracts to a configuration corresponding to configuration 203 of FIG. 2, which enables to remove it.

Thus, the placing of the stent may be performed without heating and the stent removal comprises a heating step.

Specific embodiments have been described. Various alterations, modifications, and improvements will readily occur to those skilled in the art.

In particular, the described embodiments are not limited to the specific stent structures described in relation with FIGS. 2 to 5. It will be within the abilities of those skilled in the art to adapt the provided solution to other stent types, for example, stents using a meshing rather than a simple filiform element, or stent comprising a helical band rather than a helical wire.

More generally, it will be within the abilities of those skilled in the art to adapt the provided solution to all types of stents, in the medical field or in other fields.

Further, the described embodiments are not limited to the case where the shape-memory materials are nickel-titanium alloys. Other shape-memory materials may be used, such as for example certain alloys based on copper and/or on aluminum and/or on nickel and/or on zinc, a titanium/niobium alloy, etc.

Further, the described embodiments are not limited to a double shape-memory stent. Based on the teachings of the present disclosure, it will also be within the abilities of those skilled in the art to form stents where a number of memory shapes greater than two is memorized.

The invention claimed is:

1. A stent comprising a filiform element, this element comprising, in transversal cross-section, a first portion made of a shape-memory metal alloy and a second portion made of a shape-memory metal alloy, the first and second portions having different shape-memory properties,
   wherein the first portion has a first activation temperature, and the second portion has a second activation temperature higher than the first temperature,
   and wherein the first and second portions are arranged so that the stent takes a first expanded configuration when the first portion is activated, and a second contracted configuration when the second portion is activated.

2. The stent of claim 1, wherein at least one section of the stent has an approximately generally cylindrical shape having a first diameter in the first configuration and a second diameter smaller than the first diameter in the second configuration.

3. The stent of claim 1, wherein the filiform element has a generally helical shape.

4. The stent of claim 1, wherein said element has the shape of a diabolo.

5. The stent of claim 1, wherein the first portion is a hollow wire, and wherein the second portion is a wire of smaller diameter arranged within the hollow wire.

6. The stent of claim 1, wherein the first and second portions are different areas of the cross-section of a same wire.

7. The stent of claim 1, wherein the shape-memory alloy of the first and/or the second portion is an alloy based on nickel and titanium.

8. The stent of claim 1, wherein said filiform element comprises at its ends contact terminals enabling to circulate an electric current in the first and/or second portions.

9. The stent of claim 1, further comprising a silicone coating.

10. The stent of claim 6, wherein the filiform element is formed from a wire initially made of a single metal alloy, the wire being first globally treated such that both the first and second portions acquire the same shape-memory properties, and then locally treated to modify the shape-memory properties of only the second portion.

\* \* \* \* \*

UNITED STATES PATENT AND TRADEMARK OFFICE
CERTIFICATE OF CORRECTION

PATENT NO. : 9,918,856 B2
APPLICATION NO. : 14/900346
DATED : March 20, 2018
INVENTOR(S) : Denis Favier et al.

Page 1 of 1

It is certified that error appears in the above-identified patent and that said Letters Patent is hereby corrected as shown below:

On the Title Page

Item (73) Assignees are hereby amended as follows:
(73) Assignee:  University Grenoble Alpes, Saint martin D' Heres (FR)
Assistance Publique - Hopitaux DE, Paris (FR)
Centre National De La Recherche Scientifique, Paris (FR)

Signed and Sealed this
Twenty-seventh Day of November, 2018

Andrei Iancu
*Director of the United States Patent and Trademark Office*